(12) United States Patent
Walsh

(10) Patent No.: US 11,999,357 B2
(45) Date of Patent: Jun. 4, 2024

(54) VEHICLE-BASED WELLNESS DIAGNOSTIC PLATFORM

(71) Applicant: Endera Corporation, Casper, WY (US)

(72) Inventor: John Joseph Walsh, Casper, WY (US)

(73) Assignee: Endera Corporation, Casper, WY (US)

( * ) Notice: Subject to any disclaimer, the term of this patent is extended or adjusted under 35 U.S.C. 154(b) by 232 days.

(21) Appl. No.: 17/543,437

(22) Filed: Dec. 6, 2021

(65) Prior Publication Data

US 2022/0176970 A1 Jun. 9, 2022

Related U.S. Application Data

(60) Provisional application No. 63/122,879, filed on Dec. 8, 2020.

(51) Int. Cl.
| | |
|---|---|
| *B60W 40/08* | (2012.01) |
| *A61B 5/00* | (2006.01) |
| *A61B 5/01* | (2006.01) |
| *G06Q 10/02* | (2012.01) |
| *G06V 20/58* | (2022.01) |
| *G06V 40/10* | (2022.01) |

(Continued)

(52) U.S. Cl.
CPC .............. *B60W 40/08* (2013.01); *A61B 5/01* (2013.01); *A61B 5/6893* (2013.01); *G06Q 10/02* (2013.01); *G06V 20/58* (2022.01); *G06V 40/103* (2022.01); *G06V 40/171* (2022.01); *G06V 40/67* (2022.01); *B60W 2300/10* (2013.01); *B60W 2540/041* (2020.02); *B60W 2540/221* (2020.02)

(58) Field of Classification Search
CPC ........... B60W 40/08; B60W 2540/041; B60W 2540/221; B60W 2300/10; G06V 20/58; G06V 40/67; G06V 40/171; G06V 40/103; A61B 5/01; A61B 5/6893; G06Q 10/02
USPC .......................................................... 340/576
See application file for complete search history.

(56) References Cited

U.S. PATENT DOCUMENTS

| | | | | |
|---|---|---|---|---|
| 4,774,226 | A * | 9/1988 | Lewenstein ............ | A61K 39/36 514/3.3 |
| 5,915,268 | A * | 6/1999 | Linker .................... | G01V 9/007 73/28.01 |
| 9,693,695 | B1 * | 7/2017 | Dolph .................. | A61B 5/7278 |

(Continued)

*Primary Examiner* — Zhen Y Wu
(74) *Attorney, Agent, or Firm* — Rutan & Tucker, LLP

(57) ABSTRACT

A wellness diagnostic platform installed on a vehicle to identify potential passengers with evident symptoms of a contagious illness is described. The wellness diagnostic platform includes a wellness monitoring unit and a boarding confirmation unit. The wellness monitoring unit includes a camera and/or one or more thermal sensors. The camera may capture physical characteristics of the potential passenger to determine health and the thermal sensors can measure a temperature of the potential passenger prior to boarding the vehicle. The boarding confirmation unit is configured to receive at least a display object identifying a diagnostic result computed by the wellness monitoring unit that the potential passenger is (i) advised to board the vehicle when a temperature of the potential passenger is equal to or below a prescribed temperature threshold or (ii) advised to refrain from boarding the vehicle when the temperature of the potential passenger exceeds prescribed temperature threshold.

13 Claims, 16 Drawing Sheets

(51) Int. Cl.
*G06V 40/16* (2022.01)
*G06V 40/60* (2022.01)

(56) References Cited

U.S. PATENT DOCUMENTS

| | | | | |
|---|---|---|---|---|
| 10,671,852 | B1* | 6/2020 | Zadeh | G06F 3/00 |
| 2004/0166550 | A1* | 8/2004 | Sullivan | G01N 33/53 |
| | | | | 435/7.94 |
| 2011/0260026 | A1* | 10/2011 | Ye | F16M 11/04 |
| | | | | 248/298.1 |
| 2012/0122075 | A1* | 5/2012 | Call | B01D 45/04 |
| | | | | 422/62 |
| 2013/0130227 | A1* | 5/2013 | Peltz | C12M 41/48 |
| | | | | 435/286.1 |
| 2017/0270348 | A1* | 9/2017 | Morgana | H04N 23/611 |
| 2018/0018593 | A1* | 1/2018 | Benavides | G08B 21/0288 |
| 2018/0376072 | A1* | 12/2018 | Kwon | H04N 23/63 |
| 2022/0020481 | A1* | 1/2022 | Luthra | G06Q 50/265 |
| 2022/0036395 | A1* | 2/2022 | Huang | G06V 40/166 |

* cited by examiner

VEHICLE-BASED WELLNESS DIAGNOSTIC PLATFORM

CROSS-REFERENCE TO RELATED APPLICATIONS

This application claims the benefit of priority on U.S. Provisional Application No. 63/122,879 filed Dec. 8, 2020, the entire contents of which are incorporated by reference herein.

FIELD

Embodiments of the disclosure relate to the field of vehicle services, and more specifically, one embodiment of the disclosure relates a wellness diagnostic platform that leverages thermal sensors and/or other health-monitoring components to provide a safe environment within a multi-passenger vehicle.

GENERAL BACKGROUND

Avoidance of the spread of illness is a serious worldwide issue, particularly in the United States. Given the COVID-19 pandemic, a larger segment of the population is now experiencing concerns about occupying enclosed spacing with persons unknown to them, as these persons may have the COVID-19 virus or another contagious illness such as the flu. These concerns have greatly impacted the use of multi-passenger transportation, including public transportation.

Multi-passenger transportation provides many benefits to individuals, communities, and the local economy. For example, while so much attention has been focused on the electric car movement, public transportation and other multi-passenger transportation services provide greater benefits in reducing air pollution and traffic congestion that have plagued certain cities, especially in those areas surrounding airports. As greater use of multi-passenger transportation may assist in mitigating global climate change and overcrowded streets, a system is now needed to provide assurances to passengers that the use of such transportation poses little-to-no health risks.

BRIEF DESCRIPTION OF THE DRAWINGS

Embodiments of the invention are illustrated by way of example and not by way of limitation in the figures of the accompanying drawings, in which like references indicate similar elements and in which.

DETAILED DESCRIPTION

Figure 1A:
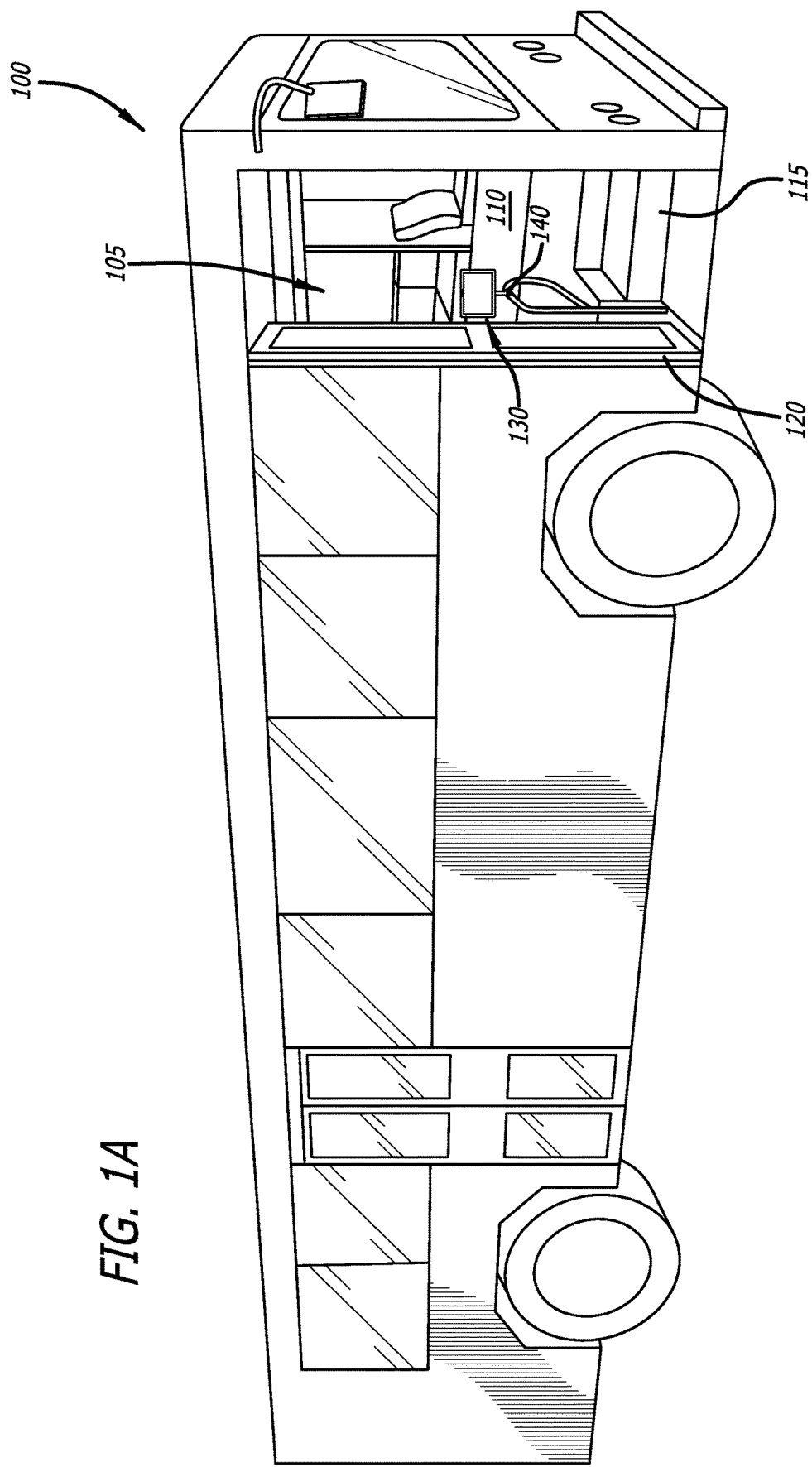
FIG. 1A is a first exemplary embodiment of a vehicle deploying a wellness diagnostic platform.

According to one embodiment of the disclosure, a vehicle-based wellness diagnostic platform is described. According to one embodiment of the disclosure, the wellness diagnostic platform is deployed to provide an ancillary service to identify and/or prevent passengers with evident symptoms of a contagious illness (e.g., fever, etc.) from boarding a multi-passenger vehicle and riding within in the vehicle's enclosed interior space. Herein, according to one embodiment of the disclosure, the wellness diagnostic platform features a wellness monitoring unit and a boarding confirmation unit.

The wellness monitoring unit features components that conduct health-based diagnostics of a passenger to confirm that the passenger is not exhibiting symptoms consistent with certain infectious diseases. For example, according to this embodiment, the wellness monitoring unit may feature one or more thermal sensors to measure a temperature of a potential passenger prior to boarding. When the measured temperature of the potential passenger at least is equal to or falls below a prescribed temperature threshold, the potential passenger is granted permission to board the multi-passenger vehicle. In particular, a first type of display object is rendered on a display screen of the wellness monitoring unit to notify the potential passenger that she or he is permitted to board the multi-passenger vehicle. Otherwise, where the measured temperature exceeds the prescribed temperature threshold, a second type of display object (different than the first display object) is rendered on the display screen of the wellness monitoring unit to notify the potential passenger that she or he is not permitted to board the multi-passenger vehicle. As an option, the potential passenger may be provided information for available alternative methods of conveyance (e.g., specifically configured vehicle with operator isolated from the passengers by a partition, rear side door entry, partitioned seats with barriers there between, etc.).

It is contemplated that, in lieu of a measured temperature, other characteristics of the potential passenger may be analyzed. For example, the wellness monitoring unit may include cameras to capture images of the potential passenger and, upon being processed by software, most notably software based on artificial intelligence (AI) software or trained machine learning for example, the images may detect specific characteristics of the potential passenger that are systematic of a contagious illness. These specific characteristics may be directed to, but are not limited or restricted to skin, eyes and mouth characteristics. For example, pale lips or pace skin around the face may identify the potential passenger as being ill. Furthermore, other characteristics may include a swollen face, droopy corners of the mouth, hanging eyelids, and/or discolored (red) eyes.

Concurrently, at least the display object is transmitted from the wellness monitoring unit to the boarding confirmation unit for display. Besides the display object, a captured image of the potential passenger may be transmitted as well. Upon reviewing the boarding confirmation unit, the operator of the vehicle is able to discern what passengers are permitted or precluded from boarding the vehicle, and in some case, may need to intervene and ask a potential passenger to seek alternative arrangements that may be available to passengers with monitored symptoms of illness (hereinafter, "unwell passenger").

Herein, different embodiments of the wellness diagnostic platform are described. In one embodiment, the diagnosis of the potential passenger for certain symptoms of illness requires the vehicle doors to be opened to provide a line-of-sight to conduct health-based measurements of the potential passenger. Alternatively, in another embodiment, the diagnosis of the potential passenger for certain illness symptoms may be accomplished while the vehicle doors remain closed, where the vehicle doors are opened after the first potential passenger is cleared to board or are repeatedly opened/closed to allow only the scanned potential passenger to board.

I. Terminology

In the following description, certain terminology is used to describe aspects of the invention. In certain situations, the terms "unit" and "component" are representative of hardware, firmware, and/or software that is configured to perform one or more functions. As hardware, the unit (or component) may include circuitry having data processing or storage functionality. Examples of such circuitry may include, but are not limited or restricted to a microprocessor, one or more processor cores, a programmable gate array, a microcontroller, an application specific integrated circuit, wireless receiver, transmitter and/or transceiver circuitry, semiconductor memory, or combinatorial elements (AND gates, OR gates, NOR gates, NAND gates, or the like).

Alternatively, or in combination with the hardware circuitry described above, the unit (or component) may be software in the form of one or more software modules. The software modules may include an executable application, a daemon application, an application programming interface (API), a subroutine, a function, a procedure, a plug-in, an applet, a servlet, a routine, source code, a shared library/dynamic load library, or one or more instructions. The software module(s) may be stored in any type of a suitable non-transitory storage medium, or transitory storage medium (e.g., electrical, optical, acoustical or other form of propagated signals such as carrier waves, infrared signals, or digital signals). Examples of non-transitory storage medium may include, but are not limited or restricted to a programmable circuit; a semiconductor memory; non-persistent storage such as volatile memory (e.g., any type of random access memory "RAM"); persistent storage such as non-volatile memory (e.g., read-only memory "ROM", power-backed RAM, flash memory, phase-change memory, etc.), a solid-state drive, hard disk drive, an optical disc drive, or a portable memory device. As firmware, the executable code may be stored in persistent storage.

A "vehicle" generally refers to a multi-passenger conveyance such as an automotive conveyance (e.g., shuttle van, a bus, a limousine, etc.) an airplane, a train, or the like. The automotive conveyance may be a low-emission, plug-in vehicle such as an electric shuttle, electric bus, or the like. However, it is contemplated that the conveyances may include an internal combustion engine.

The term "message" generally refers to signaling (wired or wireless) such as information placed in a prescribed format for transmission (or access) in accordance with a suitable delivery protocol or a suitable logical data structure such as an Application Programming Interface (API). Various examples of delivery protocols may include, but are not limited or restricted to HTTP (Hypertext Transfer Protocol); HTTPS (HTTP Secure); Simple Mail Transfer Protocol (SMTP); iMESSAGE; or Instant Message Access Protocol (IMAP). Examples of logical data structures may include HTTP APIs. Each message may be in the form of one or more packets, frames, or any other series of bits having the prescribed, structured format.

The term "meta-information" generally refers to a collection of information associated with the primary data included in the message. For example, where the message includes an image of a potential passenger, the meta-information may include, but are not limited or restricted to information pertaining to: (a) a measured temperature of the potential passenger, (b) a health state of the potential passenger; and/or (c) a boarding status assigned to the potential passenger (e.g., grant, denial).

The term "computerized" generally represents that any corresponding operations are conducted by hardware in combination with software and/or firmware. The term "concurrently" generally represents two operations being performed at least partially overlapping in time. Also, in certain instances, the terms "compare," "comparing," "comparison," or other tenses thereof generally mean determining if a match (e.g., identical or a prescribed level of correlation) is achieved between two items where one of the items may include content pertaining to meta-information that is associated with an email message being analyzed.

The term "transmission medium" generally refers to a physical or logical communication link (or path) between two units such as the wellness diagnostic unit and the boarding confirmation unit. For instance, as a physical communication path, wired and/or wireless interconnects in the form of electrical wiring, optical fiber, cable, bus trace, or a wireless channel using infrared or radio frequency (RF), may be used. The logical communication link may be any software-to-software communication scheme that supports communications between multiple (two or more) software modules or running processes.

Finally, the terms "or" and "and/or" as used herein are to be interpreted as inclusive or meaning any one or any combination. As an example, "A, B or C" or "A, B and/or C" mean "any of the following: A; B; C; A and B; A and C; B and C; A, B and C." An exception to this definition will occur only when a combination of elements, functions, steps or acts are in some way inherently mutually exclusive.

As this invention is susceptible to embodiments of many different forms, it is intended that the present disclosure is to be considered as an example of the principles of the invention and not intended to limit the invention to the specific embodiments shown and described.

II. Wellness Diagnostic Platform Architecture—First Embodiment

Referring to FIG. 1A, an exemplary embodiment of a vehicle 100 deploying a wellness diagnostic platform 110 for use in identifying potential passengers with illness symptoms to avoid possible contagion by passenger within a multi-passenger vehicle 100 is shown. Herein, the vehicle 100 is illustrated as a shuttle bus with an interior 105 that provides seating for multiple passengers. Entry into the interior 105 of the vehicle 100 is enabled and precluded by an automatic door 120 that is controlled by an operator of the vehicle 100.

Prior to entry into the vehicle 100, however, a wellness monitoring unit 130 of the wellness diagnostic platform 110 is positioned within the interior 105 of the vehicle 100 facing the automatic door 120. The positioning of the wellness monitoring unit 130 enables a potential passenger to be monitored prior to entry into the interior 105 of the vehicle 100. As shown, the wellness monitoring unit 130 may be installed on an interior railing 140, which is positioned on an edge of a stairway 115 adjacent to the automatic doors 120. Alternatively, the wellness monitoring unit 130 may be installed any portion of the interior of the vehicle 100 (e.g., mounted to a ceiling about the stairway 115, mounted to an interior wall proximate to the stairway 115, or the like.

Figure 1B:
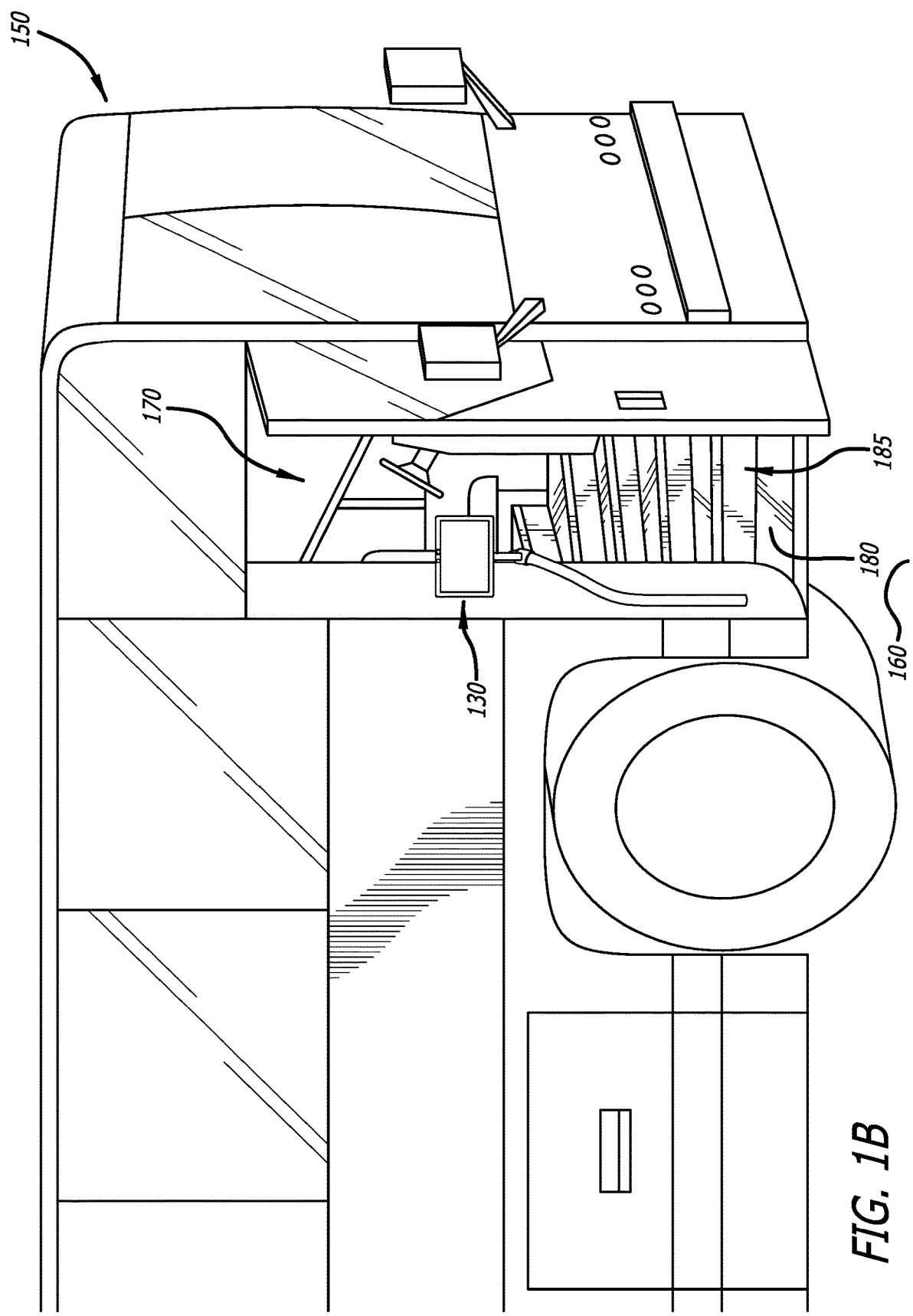
FIG. 1B is an exemplary embodiment of another type of vehicle deploying the wellness diagnostic platform of FIG. 1A.

Although the vehicle 100 is depicted as a shuttle bus, it is contemplated that the vehicle 100 may be any of a variety of conveyances. For instance, the vehicle may be a train or train (locomotive or light rail) that holds multiple persons in which the wellness monitoring unit 130 may be located on the conveyance prior to or immediately at the entry of the vehicle. Alternatively, the vehicle 100 may be a long-distance or touring bus 150 as shown in FIG. 1B, where the wellness monitoring unit 130 is positioned prior to or at an initial stage of entry by the potential. With this deployment, the wellness monitoring unit 130 is arranged to conduct health-based measurements of a passenger when the passenger is standing on the ground 160 prior to entry into an interior 170 of the vehicle 150 or is standing on a first step 180 of the stairway 185.

Figure 2A:
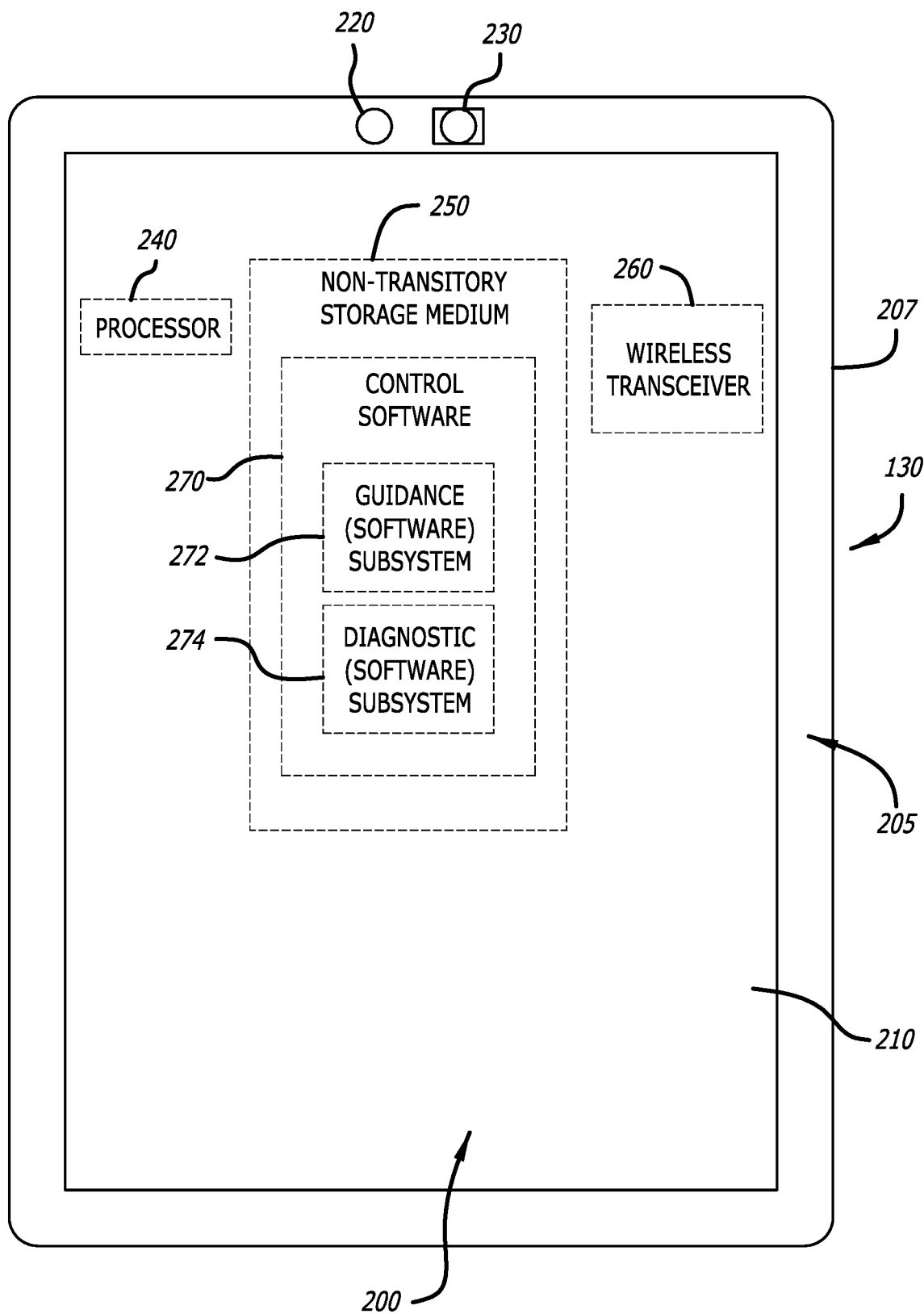
FIG. 2A is a front side view of an exemplary embodiment of the wellness monitoring unit of FIG. 1A.

Referring now to FIG. 2A, an exemplary embodiment of a front side 200 of the wellness monitoring unit 130 is shown. Herein, the wellness monitoring unit 130 may be deployed as a tablet that features a housing 205 to encase circuitry that controls operability of the wellness monitoring unit 130. A display screen 210 is visible at the front side 200 of the wellness monitoring unit 130, where the display screen 210 is provided to display an image or series of images operating as a video feed (generally referred to as an "image") of a face of the potential passenger that is captured by a camera 220 mounted along a bezel 207 of the housing 205. Mounted along the bezel 207 of the housing 205 proximate to the camera 220, a thermal sensor 230 is provided to conduct a thermal scan of area of the potential passenger's face when she or he is positioned appropriately as set forth in FIGS. 3A-3B.

Referring still to FIG. 2A, the wellness monitoring unit 130 includes a processor 240, a non-transitory storage medium 250 and/or a wireless transceiver 260, which are encased or at least partially encased within the housing 205. The non-transitory storage medium 250 includes control software 270, which controls operability of the wellness monitoring unit 130. For example, the control software 270 is configured with a guidance (software) subsystem 272 configured to generate and display indicia that guides a potential passenger to reposition herself in front of the thermal sensor 230 and a diagnostic (software) subsystem 274 configured to (i) activate the thermal sensor 230 that conducts a thermal scan to measure the temperature of the potential passenger and (ii) determine, based on the measured temperature, whether the potential passenger is cleared to board the vehicle.

Figure 4A:
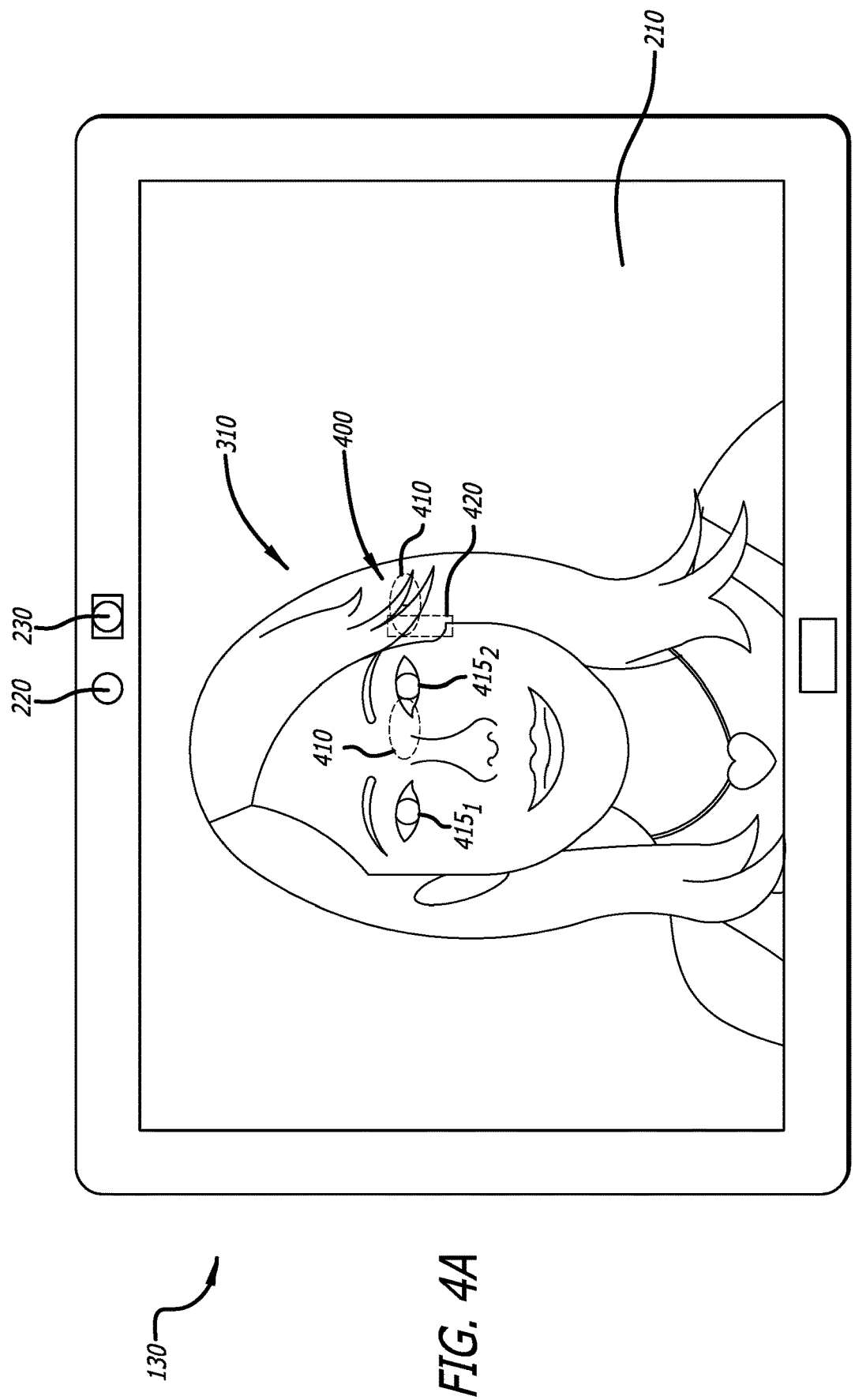
FIG. 4A is an exemplary embodiment of a display objects generated by a guidance subsystem operating as part of the control software.
Figure 4B:
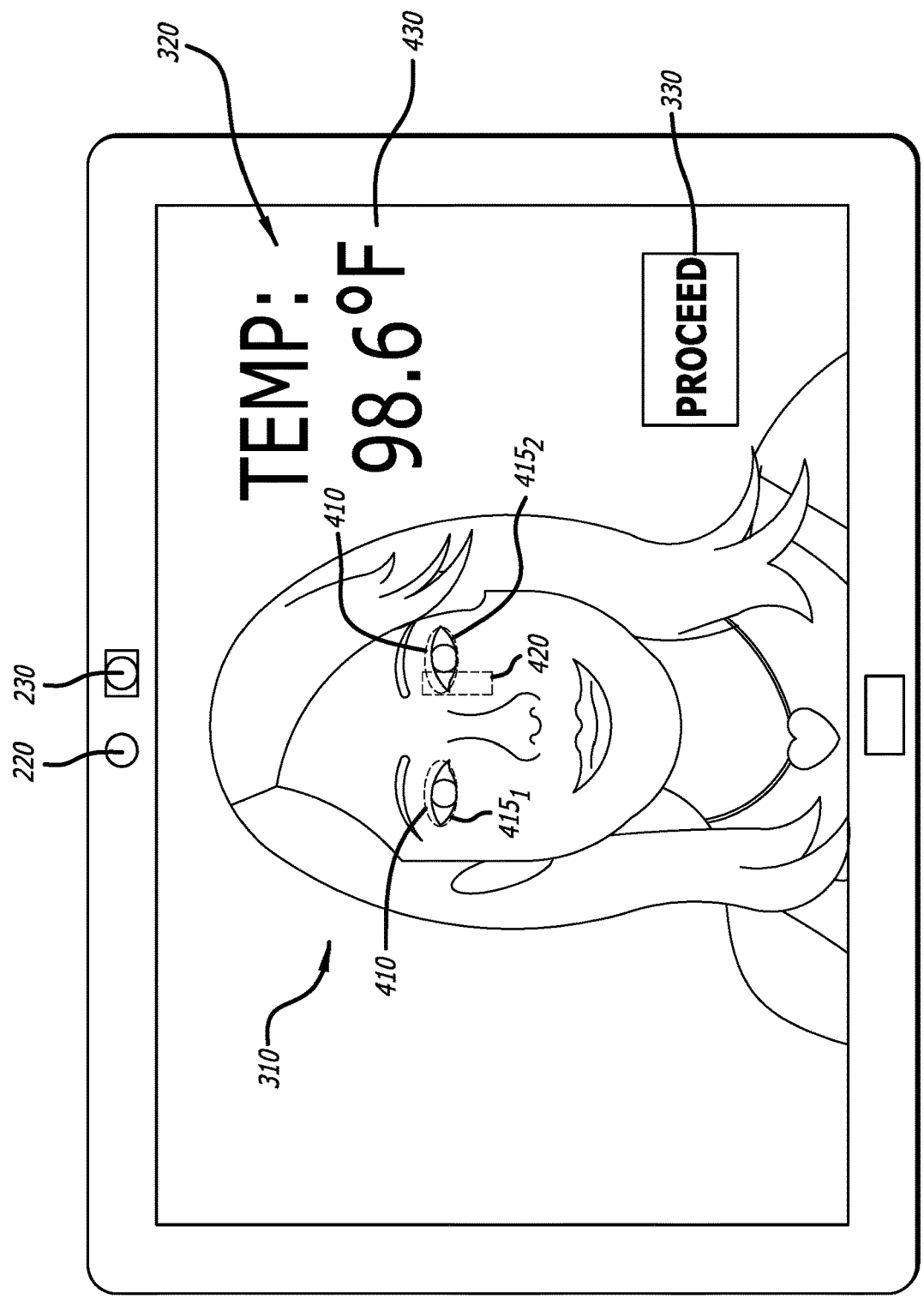
FIG. 4B is an exemplary embodiment of the display objects generated by the guidance subsystem in which the potential passenger alters her orientation in accordance with the display objects.
Figure 4C:
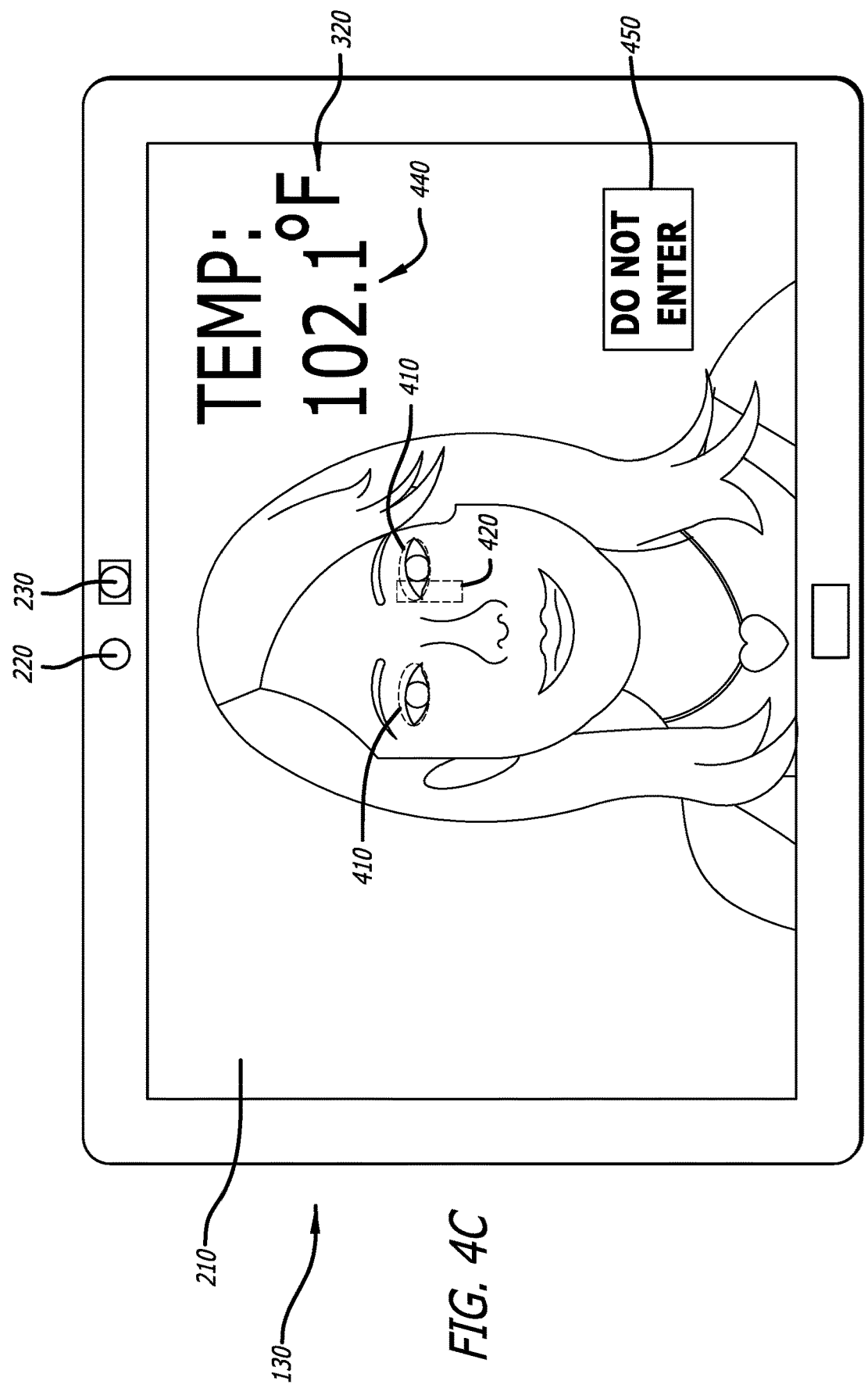
FIG. 4C is an exemplary embodiment of a display screen of the wellness monitoring unit based on analytics results, determined by the a diagnostic subsystem of the wellness monitoring unit, which identifies whether the potential passenger is well and permitted to board the vehicle.

According to one embodiment of the disclosure, the control software 270 is configured to activate the camera 220 and activate the guidance subsystem 272, which generates indicia (e.g., one or more display objects) that are rendered to overlay the image of the potential passenger's face. As shown in FIGS. 4A-4C, the guidance indicia may include (i) a first display object that is rendered for alignment with certain features of the passenger's face and (ii) a second display object that is rendered and positioned to identify a scanning location for the thermal sensor 230. An optional third display object (e.g., directing indicating images such as directional arrows, textual description, etc.) may be generated by the guidance subsystem 272 of the control software 270 and subsequently rendered to instruct a potential passenger to move her or his head until the first display object is substantially aligned with the second display object.

The diagnostic subsystem 274 of the control software 270 is further configured to activate the thermal sensor 230 to conduct a thermal scan (reading) of the potential passenger to measure her or his temperature prior to boarding the vehicle 100 when targeted facial features of the passenger are aligned with the first display object, as described below. The diagnostic subsystem 274 is configured to determine, based on the measured temperature, whether the potential passenger is permitted to board (i.e., the measured temperature falls below a prescribed temperature threshold that is normally associated with an unwell potential passenger). The measured temperature and the determined results are displayed, less than a few seconds after the scan by the thermal sensor 230, on the display screen 210 to advise the potential passenger accordingly.

The wireless transceiver 260 is configured to transmit an image of the potential passenger at the time of the thermal scan along with the determined results (and/or the measured temperature) to the boarding confirmation unit accessible (or visible) by the operator of the vehicle. According to one embodiment of the disclosure, the uploaded data to the boarding confirmation unit enables the operator to determine whether a passenger has an elevated temperature, and if not, to allow the potential passenger to board the vehicle. In the event that the potential passenger is detected to have an elevated temperature by the wellness monitoring unit 130, the operator would be notified and may, if necessary, request the passenger to deboard the vehicle.

Figure 2B:
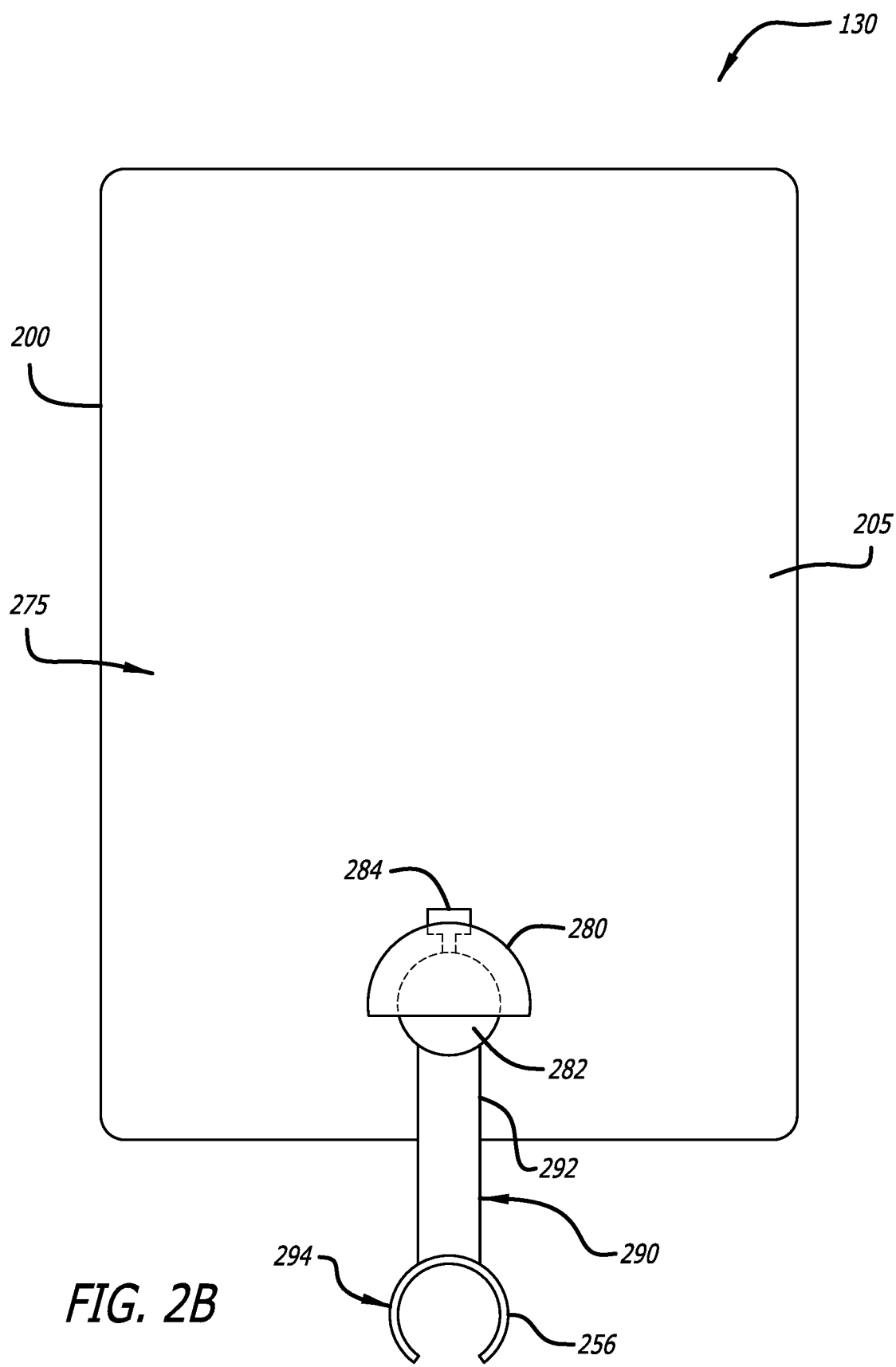
FIG. 2B is a back side view of the exemplary embodiment of the wellness monitoring unit of FIG. 1A.

Referring now to FIG. 2B, an exemplary illustration of a back side 275 of the housing 205 for the wellness monitoring unit 130 is shown. The back side 275 of the housing 205 includes a securing mechanism (e.g., socket) 280, which is structured to receive and secure a fastener 290 slidably inserted into the bracket 280. In particular, as shown, a first attachment member 292 of the fastener 290 may be inserted into an opening 282 of the securing mechanism 280 and is removably coupled thereto. The fastener 290 is secured to a component within the interior of the vehicle (e.g., the handrail 140 of FIG. 1A or FIG. 1B). As an illustrative example, the securing mechanism 280 may be deployed as a socket to receive a ball 282 at an end of the first attachment member 292. The socket 280 includes a release button 284 that, when depressed, allows removal of the ball 282 from the socket 280 after attachment.

According to one embodiment of the disclosure, the fastener 290 includes the first attachment member 292 and a second attachment member 294, which is positioned at an opposite end of the fastener 290 from the first attachment member 292. The first attachment member 292 is configured to be securely coupled to the bracket 280 upon insertion through the bracket opening 282. The second attachment member 294 may be configured in accordance with any of a plurality of attachment mechanisms to secure itself to the handrail 140. For instance, the second attachment member 294 may be a welded connection to the handrail 240 for a custom installation. Alternatively, as shown in FIG. 2B, the second attachment member 294 may operate as a clamp 296 that is specifically sized to secure surround a substantial portion of the circumference of the handrail 140 or a clamp with an adjusting band and tightening bolt, where the band surrounds the diameter of the handrail 140 and the tightening bolt can be rotated to reduce the diameter of the band.

Figure 3:
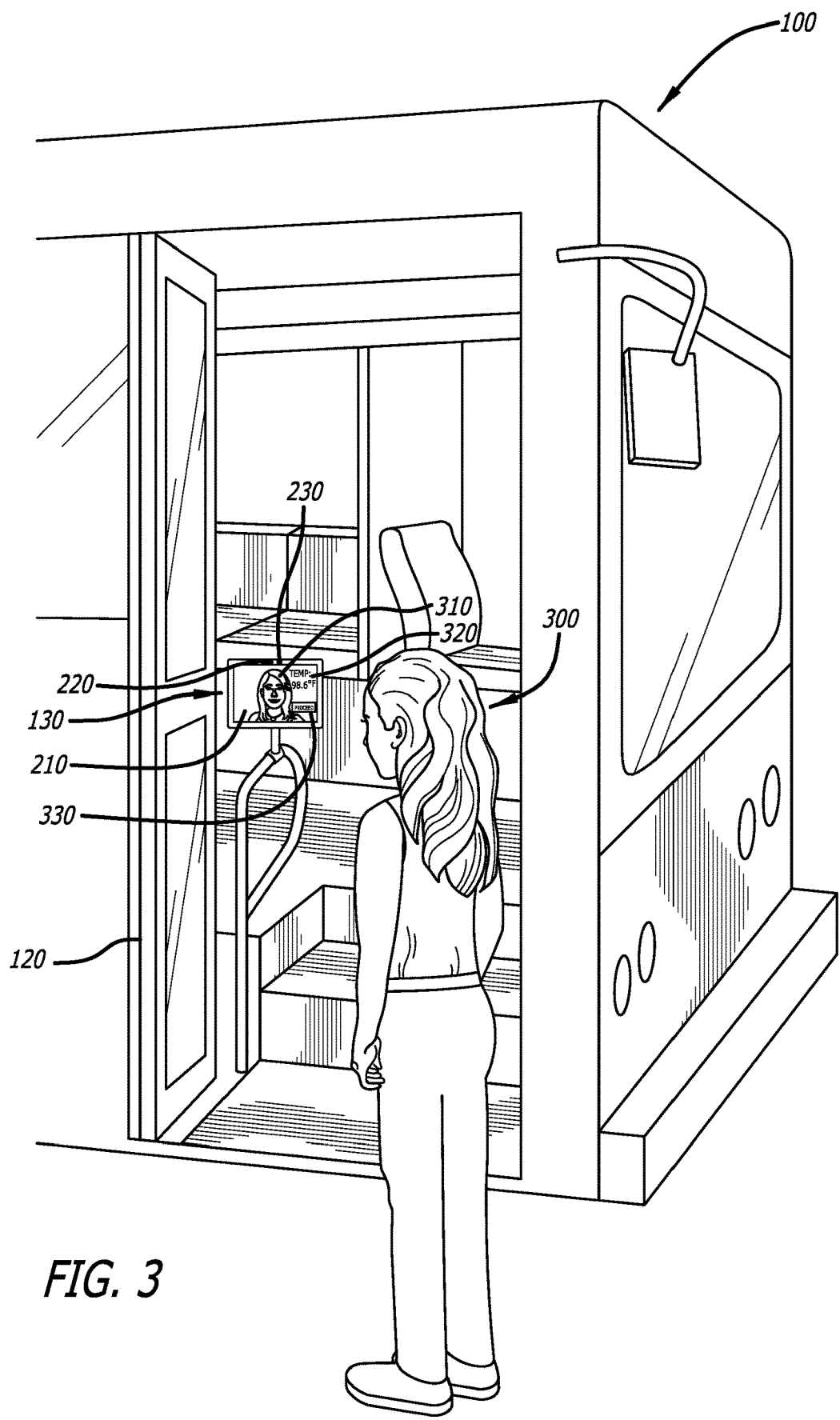
FIG. 3 is a more detailed representation of the exemplary embodiment of the wellness monitoring unit mounted within an interior of the vehicle as shown in FIG. 1A during execution of control software installed within the wellness monitoring unit.

Referring to FIG. 3, an exemplary embodiment of the wellness monitoring unit 130 mounted within the interior of the vehicle 100 to predict whether a potential passenger 300 is healthy and permitted to board the vehicle 100 is shown. Herein, the door 120 for the vehicle 100 is opened to allow a direct "line-of-sight" between the potential passenger 300 and the wellness monitoring unit 130. Thereafter, the wellness monitoring unit 130 generates one or more display objects that guide the potential passenger 300 to position herself to face the wellness monitoring unit 130 for thermal scanning prior to entry into the vehicle 100.

Referring to both FIG. 2A and FIG. 3, prior to conducting a thermal scan by the thermal sensor 230, the camera 220 of the wellness monitoring unit 130 captures and displays a facial image 310 of the potential passenger 300 on the display screen 210. Additionally, the guidance subsystem 272 of the control software 270, operating within the wellness monitoring unit 130, guides the potential passenger 300 to position herself to be captured by the camera 220 and orient her face in a position for the thermal sensor 230 to accurately conduct a scan to measure her temperature. Such guidance may be accomplished by the guidance subsystem 272 generating one or more display objects overlaying a facial image of the potential passenger 300 to move so that the thermal sensor 230 is aligned with a targeted facial area, as described below and illustrated in FIGS. 4A-4C.

Upon determining that the potential passenger 300 is appropriately positioned, the guidance subsystem 272 signals the diagnostic subsystem 274 to conduct a thermal scan to measure the temperature of the potential passenger 300 prior to boarding the vehicle. The diagnostic results 320 are illustrated on the display screen 210. Furthermore, in response to the diagnostic subsystem 274 of the wellness monitoring unit 130 determining that the measured temperature of the potential passenger 300 satisfies a first temperature threshold (e.g., measured temperature is less than or equal to ninety-nine degrees Fahrenheit (99° F.)) and/or satisfies a second temperature threshold (e.g., measured temperature is greater than 99° F.), the potential passenger 300 is notified whether or not she is permitted to board the vehicle 100. In particular, when the measured temperature satisfies the first temperature threshold (or fails to satisfy the second temperature threshold), a first type of display image 330 is rendered on the display screen 210 of the wellness monitoring unit 130 to notify the potential passenger 300 that she is permitted to board the vehicle 100. Otherwise, where the measured temperature satisfies the second temperature threshold (or fails to satisfy the first temperature threshold), a second type of display image (different than the first display image) is rendered on the display screen 210 of the wellness monitoring unit 130 to notify the potential passenger 300 that she is not permitted to board the vehicle 100.

Additionally, or in the alternative, the diagnostic subsystem 274 may be configured to analyze other characteristics of the potential passenger other than through the thermal scan. For example, the diagnostic subsystem 274 may utilize the camera 220 to capture the facial image 310 of the potential passenger 300 and, upon being processed by control software 270, which may include artificial intelligence based (AI-based) software or trained machine learning (ML) software operating within the diagnostic subsystem 274, the facial image 310 may be relied upon to detect specific characteristics of the potential passenger 300 that are systematic of a contagious illness. These specific characteristics may be directed to, but are not limited or restricted to skin, eyes and mouth characteristics. For example, pale lips or pace facial skin may constitute characteristics that identify the potential passenger 300 as being ill. Other characteristics may include, but are not limited or restricted to a swollen face, droopy corners of the mouth, hanging eyelids, and/or discolored (red, yellow) eyes. Herein, the thermal scan diagnostics will be discussed although any health diagnostic may be utilized.

Referring now to FIG. 4A, an exemplary embodiment of the wellness monitoring unit 130 deploying the guidance subsystem 272 configured to instruct how the potential passenger 300 is to orient her facial image 310 for the thermal sensor 230 to accurately capture her temperature is shown. Herein, the camera 220 is set to operate and capture the facial image 310 of the passenger prior to the passenger boarding the vehicle or captured at initial stage of such boarding. Besides the facial image 310 of the potential passenger 300, guidance indicia 400 for the potential passenger is displayed on the display screen 210 of the wellness monitoring unit 130 to position her or his face into the appropriate area. More specifically, the guidance indicia 400 may include a first display object 410, represented as bounded areas from which the potential passenger 300 is to orient her face so that her eyes $415_1$-$415_2$ are aligned with the bounded areas 410. A second display object 420, represented by another bounded area, is provided as a facial area that is proximate to one of the first display objects 410 for containing an eye (e.g., eye $415_2$) of the facial image 310. The location of the second display object 420 is selected based on a location of a person's face in which reliable temperature readings by the thermal sensor 230 typically occur.

As shown in FIG. 4B, the potential passenger 300 has oriented her facial image 310 by moving to her right so that her eyes $415_1$-$415_2$ are aligned with the first display object 410, and the second display object 420 is positioned adjacent to her right eye $415_2$. Upon determining that the eyes $415_1$-$415_2$ of the potential passenger 300 have been oriented within the first display object 410 for a prescribed period of time, the guidance subsystem of the control software, operating within the wellness monitoring unit 130, signals the diagnostic subsystem to operate. In particular, the diagnostic subsystem activates the thermal sensor 230 to conduct a thermal scan by at least measuring the temperature of the potential passenger 300 at a facial location identified by the second display object 420 and subsequently displaying a measured temperature 430 as a first set of indicia 320 on the display screen 210 along with the image 310 of the potential passenger 300. Based on whether the measured temperature satisfies the first temperature threshold (e.g., measured temperature is less than or equal to 99° F.)) that designates the user as "well," the diagnostic subsystem of the control software will generate the display image 330 that will instruct the potential passenger 300 to board the vehicle, as illustrated by the "PROCEED" display image 330 in FIG. 4B.

Similarly, as shown in FIG. 4C, where the thermal sensor 230 measures the temperature of the potential passenger 300 within the second area 420 and determines that the temperature fails to satisfy the first temperature threshold deemed to constitute the temperature of a healthy person (or determined to satisfy the second temperature threshold deemed to constitute the temperature of a person with symptoms of an illness), a measured temperature 440 is displayed as part of the first set of indicia 320. However, a different display image 450, including the indicia instruct the potential passenger 300 not to board the vehicle (e.g., indicia "DO NOT ENTER") is rendered on the display screen 210 of the wellness monitoring unit 130.

Figure 4D:
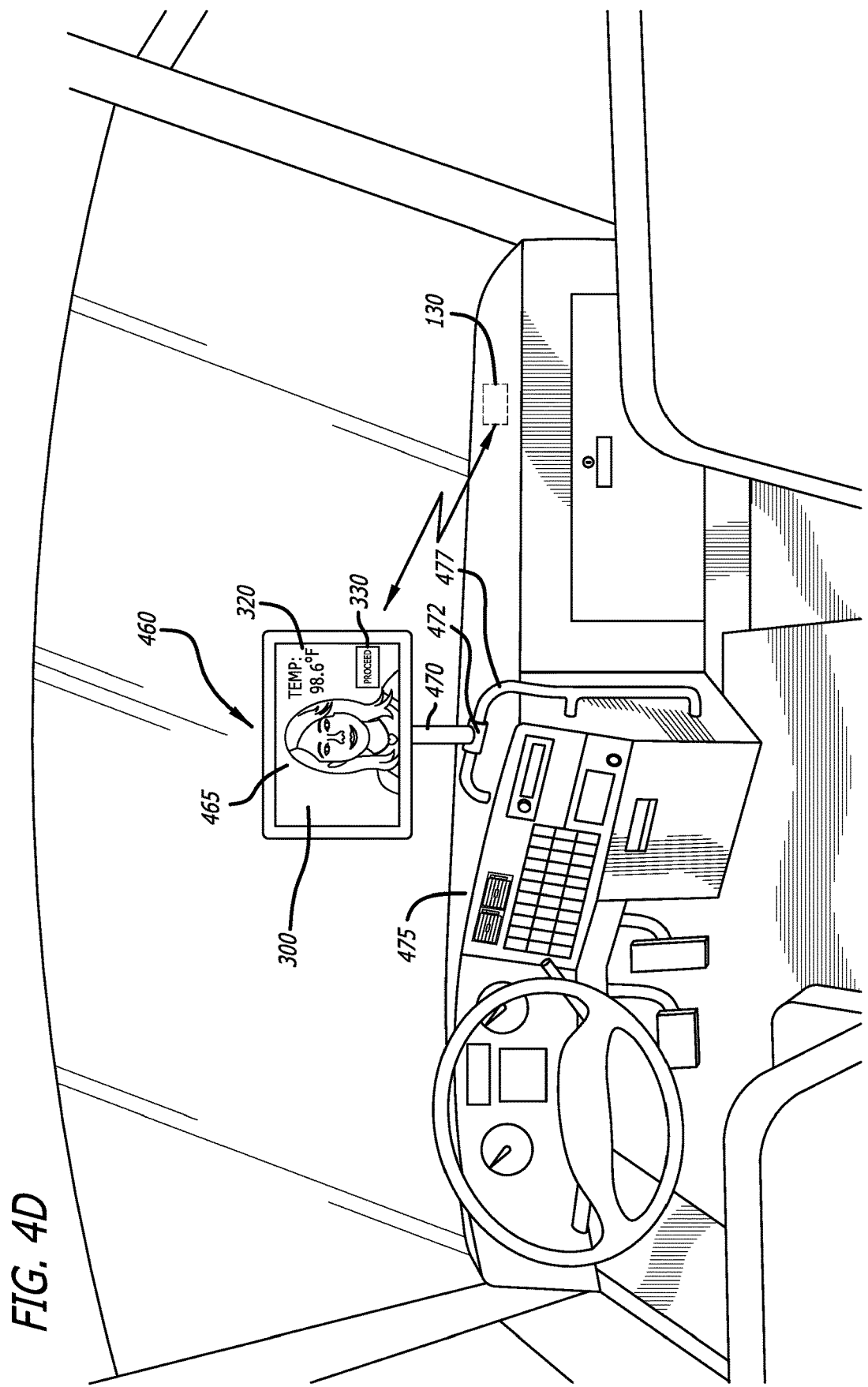
FIG. 4D is a first exemplary embodiment of a boarding confirmation unit configured to display diagnostic results generated by the diagnostic subsystem of the wellness monitoring unit.

Referring now to FIG. 4D, an illustrative embodiment of the boarding confirmation unit 460 is shown. The boarding confirmation unit 460 may be deployed as a second tablet that is communicatively coupled to the wellness monitoring unit 130 of FIGS. 1A-4C. This communicative coupling may be through Bluetooth™ or another wireless communication protocol, although a physical interconnect may be used. The boarding confirmation unit 460 renders a display image on its display screen 465 that generally replicates a display image generated by the diagnostic subsystem of the control software to advise the potential passenger that she or her is permitted to board the vehicle. As a result, the operator is able to determine whether the next expected passenger has been screened to board the vehicle.

As with the wellness monitoring unit 130, the boarding confirmation unit 460 includes an elongated attachment member 470 and a clamp 472 or other fastening member to affix to a portion of a console 475 of the vehicle 100. Herein, the portion of the console 475 may include a support bar 477 securely coupled to the console 475.

Figure 4E:
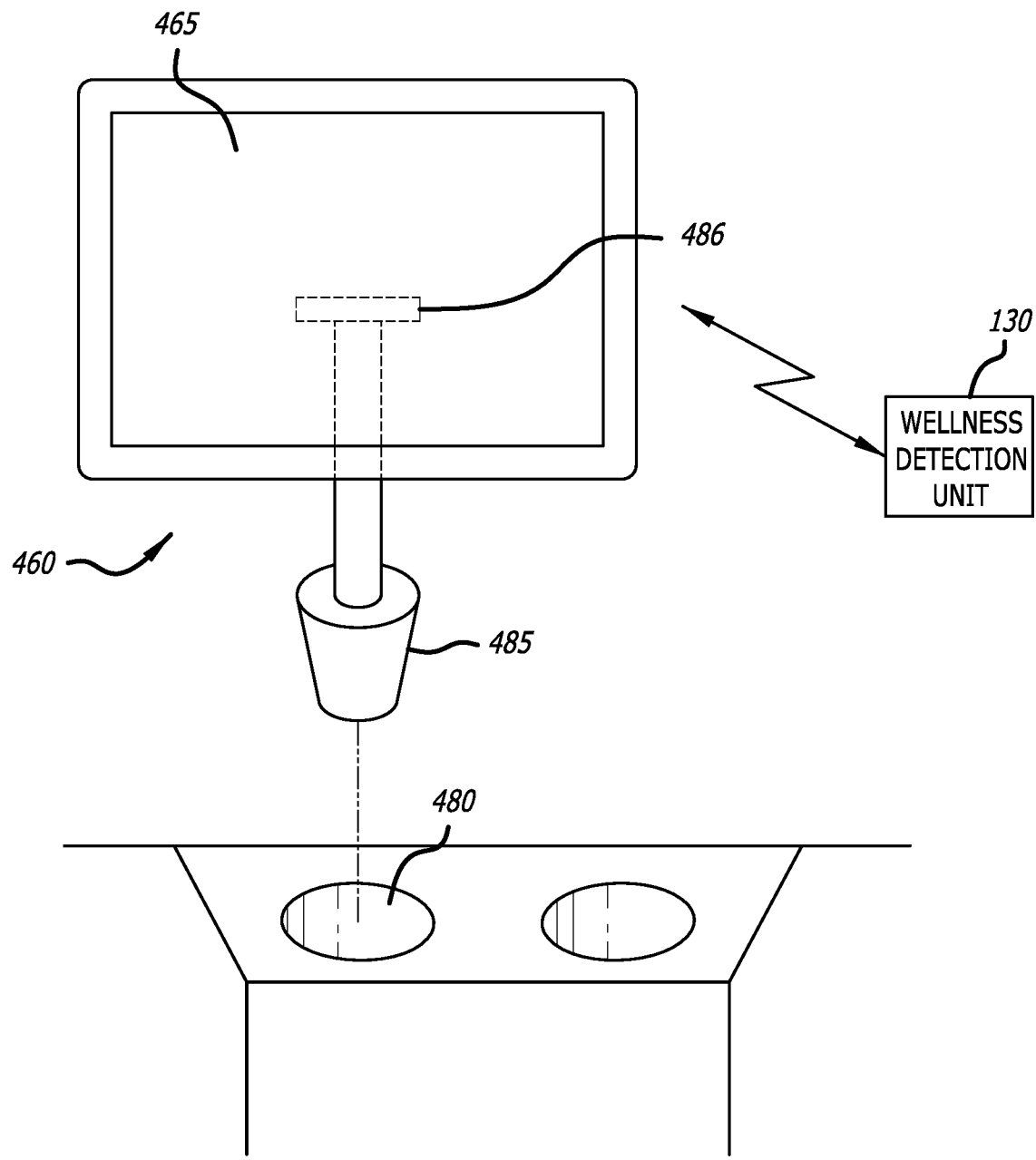
FIG. 4E is a second exemplary embodiment of a passenger boarding unit configured to display diagnostic results generated by the diagnostic subsystem of the wellness monitoring unit.

As an alternative embodiment, as shown in FIG. 4E, the boarding confirmation unit 460 may be deployed for secure insertion into a cup holder 480 in which the fastener 485 is implemented as a molded component that is sized to securely fit within the cup holder 480. Additionally, the fastener 485 may include a pivotal end 486 to allow the display screen 465 to be adjusted (e.g., vertically rotated as shown) based on the height of the operator to allow for easy viewing of the display image on the boarding confirmation unit 460.

III. Wellness Diagnostic Platform Architecture—Second Embodiment

Figure 5A:
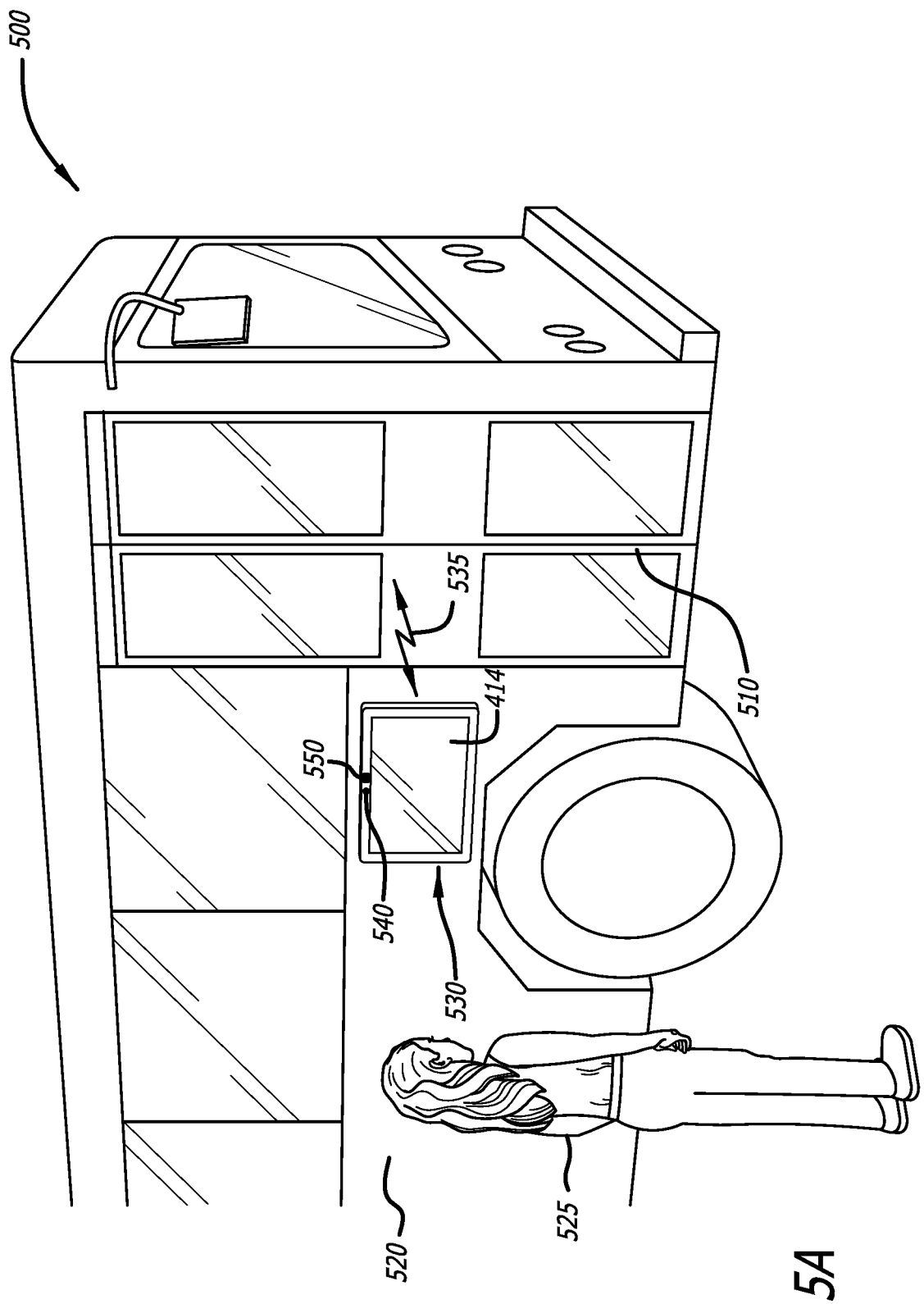
FIG. 5A is a second exemplary embodiment of a vehicle deploying a wellness monitoring unit mounted to a side panel of the vehicle.

Referring now to FIG. 5A, a second illustrative embodiment of the wellness diagnostic platform with a wellness monitoring unit 530 deployed outside of the vehicle 500 and accessible without opening of the automated doors 510 is shown. Herein, the vehicle 500 features the wellness monitoring unit 530 mounted on a side panel 520 of the vehicle 500 with a board confirmation unit (not shown) within an interior 580 (see FIG. 5B) of the vehicle 500. The wellness monitoring unit 530 includes a camera 540 and a thermal sensor 550, which operate in the same manner as the camera 220 and thermal sensor 230 of FIGS. 4A-4C. However, unlike the prior embodiment of FIGS. 1A-1B, the automated doors 510 may remain shut until the potential passenger 525 is determined to be able to board the vehicle.

Response to a determination that the measured temperature of the potential passenger 525 satisfies the first temperature threshold (e.g., passenger diagnosis as "normal"), the diagnostic subsystem of the wellness monitoring unit 530 generates and transmits a signal 535 to an electronic controller associated with the automated doors 510 or to the boarding confirmation unit (not shown) requesting the operator to open the automated doors and allow the potential passenger 525 to board. After boarding, the automated doors may be closed automatically (or by the electronic controller or operator) or the doors may remain open in which the additional potential passengers screened with a normal temperature are allowed to board the vehicle 500.

Figure 5B:
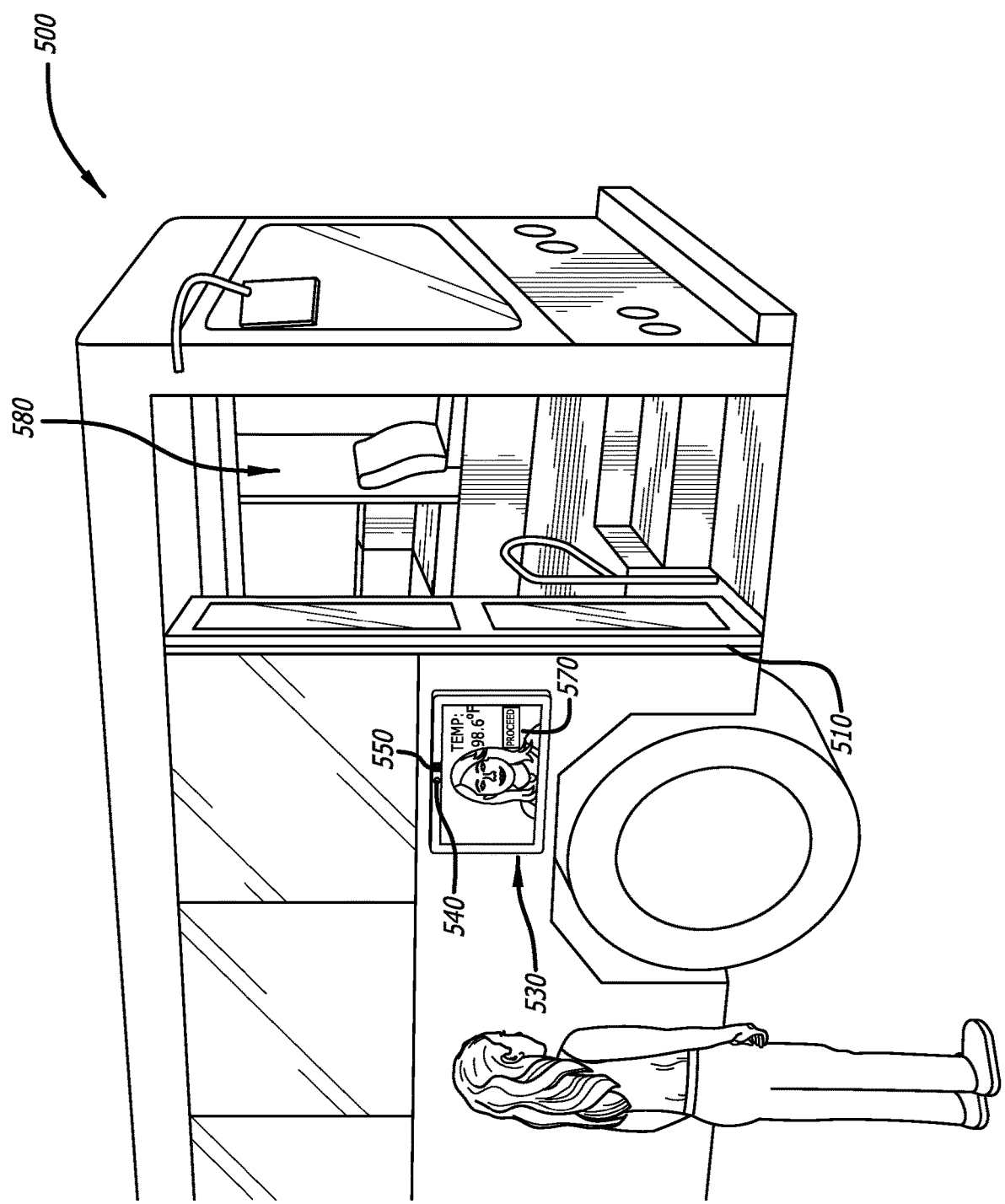
FIG. 5B is a more detailed representation of the exemplary embodiment of the wellness monitoring unit of FIG. 5A during operation.

As shown in FIG. 5B, the potential passenger 525 positions herself in the appropriate location in which the thermal sensor 550 conducts a thermal scan and measures her or his temperature. When the measured temperatures satisfies the first temperature threshold, which falls within a designated safe (healthy) temperature range, a first type of display image 570 is generated and displayed to advise the potential passenger 525 that she or he is permitted to proceed and board the vehicle 500, at which case the automated doors 510 are opened to allow the potential passenger 525 access to an interior 580 of the vehicle 500. Alternatively, when the measured temperatures falls outside the first temperature threshold (or satisfies the second temperature threshold in which the potential passenger 525 is diagnosed as unwell), a second type of display image (not shown) is generated and displayed to advise the potential passenger 525 that she is not permitted to board the vehicle 500. As a result, the automated doors 510 are closed (or remain closed) and/or the operator is notified as to which potential passenger 525 is precluded from boarding the vehicle 500.

IV. Wellness Diagnostic Platform Architecture—Third Embodiment

Figure 6A:
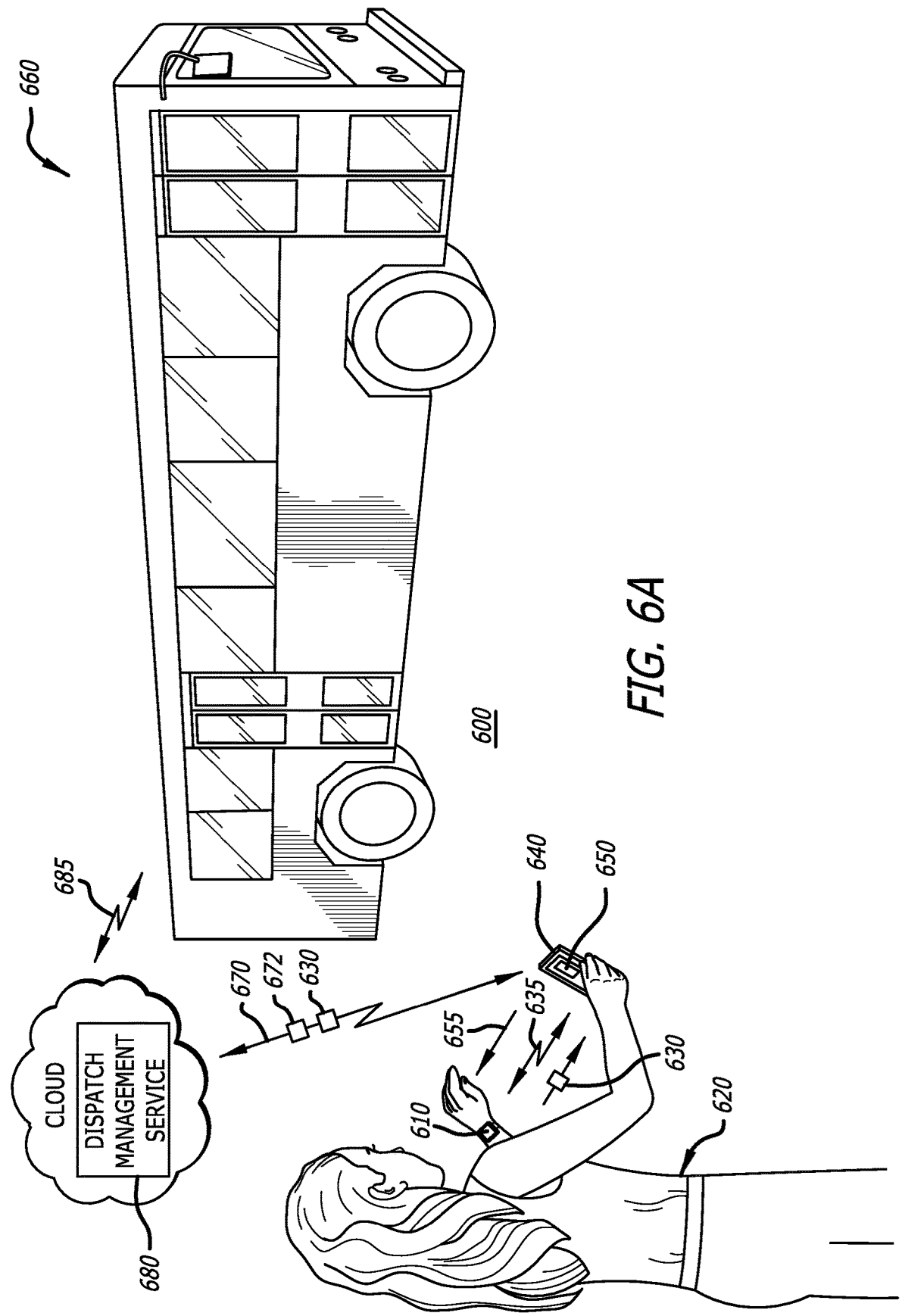
FIG. 6A is a third exemplary embodiment of a vehicle deploying a wellness diagnostic platform that is adapted to receive passenger pickup locations and confirm wellness of the potential passenger based on her or his wearable device.
Figure 6B:
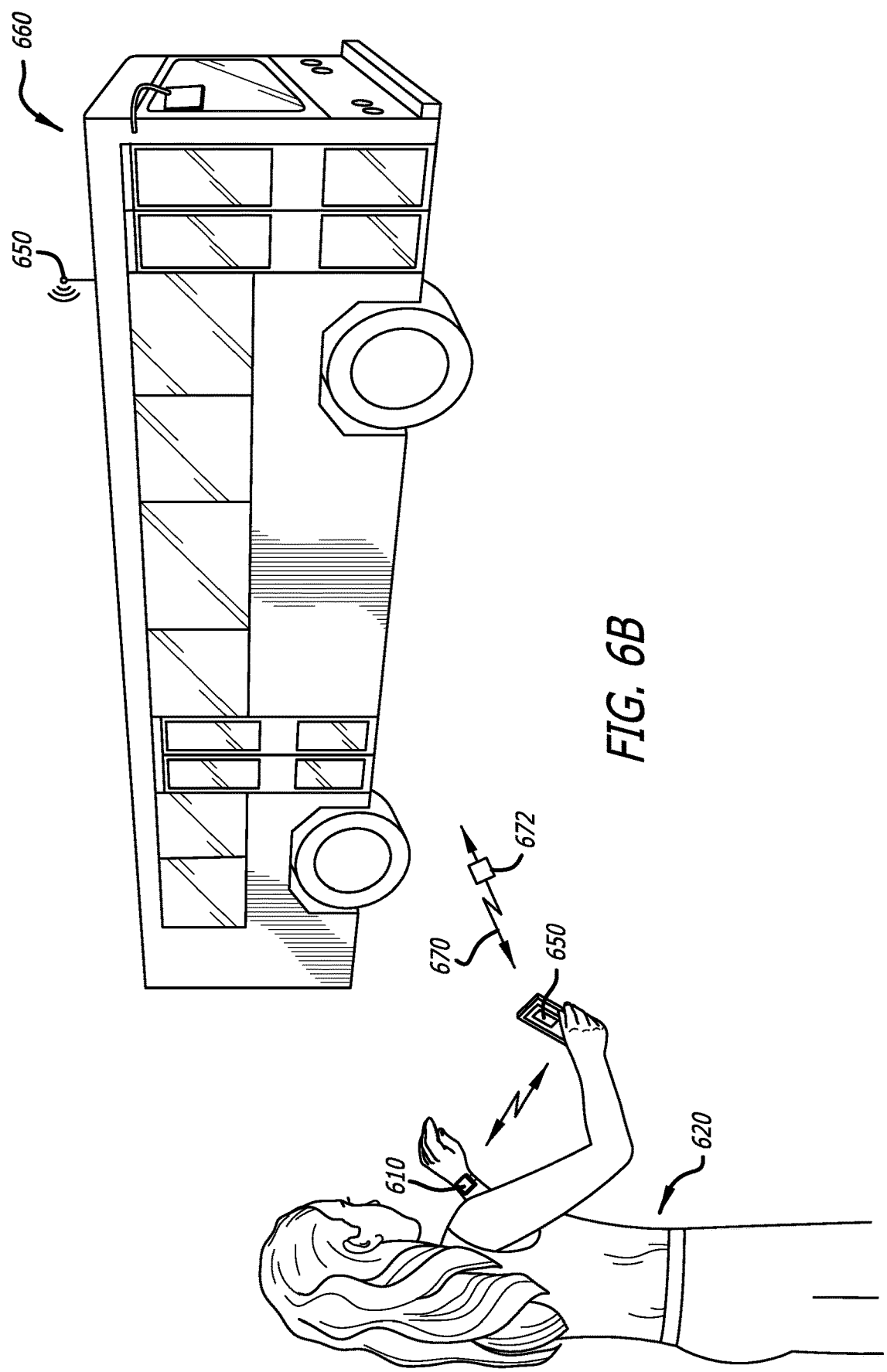
FIG. 6B is a fourth exemplary embodiment of a vehicle deploying the wellness diagnostic platform that is adapted to directly receive passenger wellness information uploaded to the boarding confirmation unit accessible to an operator of the vehicle.

Referring now to FIGS. 6A-6B, a third embodiment of a wellness diagnostic platform 600 is shown, where a wearable device 610 of the potential passenger 620 operates as a wellness monitoring unit. Herein, the wearable device 610 is configured to measure health-based data 630 associated with the potential passenger 620, including a measured temperature. The health-based data 630 may be downloaded over a wireless connection 635 (e.g., Bluetooth™ connection, cellular messaging, etc.) to a cell phone 640 of the potential passenger 620 in response to a particular event.

According to one embodiment of the disclosure, the health-based data 630 may be downloaded to a vehicle scheduling application 650, operating on the cell phone 640, in response to a first type of event, namely the activation of the vehicle scheduling application 650. In particular, upon activation, the vehicle scheduling application 650 generates and transmits a health check request message 655 over the wireless connection 635, which prompts the wearable device 610 to measure health-based data 630 associated with the potential passenger 620 and return the health-based data 630 to the vehicle scheduling application 650. The health-based data 630 may include, but is not limited or restricted to a temperature of the potential passenger 620.

Thereafter, in the event that an analysis of the health-based data 630 by the vehicle scheduling application 650 identifies that the potential passenger 620 is unwell (e.g., has an elevated temperature over a prescribed temperature threshold), the scheduling application 650 generates an alert (e.g., text message, new window identifying the potential passenger 620 has an elevated temperature and the new window with alternative transportation options is displayed, an audible playback, etc.) that indicates the potential passenger 620 is unable to reserve a seat on the multi-passenger vehicle 660. Otherwise, in the event that the analysis of the health-based data 630 by the vehicle scheduling application 650 identifies that the potential passenger 620 is well (e.g., has a normal temperature), the health-based data 630 may be included as part of a transport request message 670 to request a seat on the vehicle 660 at a prescribed time.

As further shown in FIG. 6A, the transport request message 670 is transmitted to a dispatch management service 680 operating as a cloud service. Herein, according to one embodiment of the disclosure, the transport request message 670 includes reservation data 672 (e.g., pickup time, pickup location, etc.) and/or the health-based data 630. Upon receiving the health-based data 630 associated with the potential passenger 620 as part of the transport request message 670, which includes the potential passenger's temperature captured by the wearable device 610, the dispatch management service 680 transmits a pick-up reservation message 685 to an operator of the vehicle 660. The pickup reservation message 685 may include information to advise the operator of a pickup location of the potential passenger 620 allowed to board the vehicle 660. As an alternative feature, an image of the potential passenger 620 may be captured by the vehicle scheduling application 650 to provide the operator with an image of that potential passenger 620 associated with the reservation.

Referring now to FIG. 6B, alternatively, in lieu of the vehicle scheduling application 650 providing the transport request message 670 to the dispatch management service 680 for re-routing to the vehicle 660, the vehicle 660 may include a cellular transceiver 690 or operate as a hot spot to receive the transport request message 670. For example, the transport request message 670 may constitute a cellular transmission that provides at least the reservation data 672 to the vehicle 660 determined by the vehicle scheduling application 650 to be closest in proximity to the potential passenger 620.

V. Wellness Diagnostic Platform Architecture—Fourth Embodiment

Figure 7A:
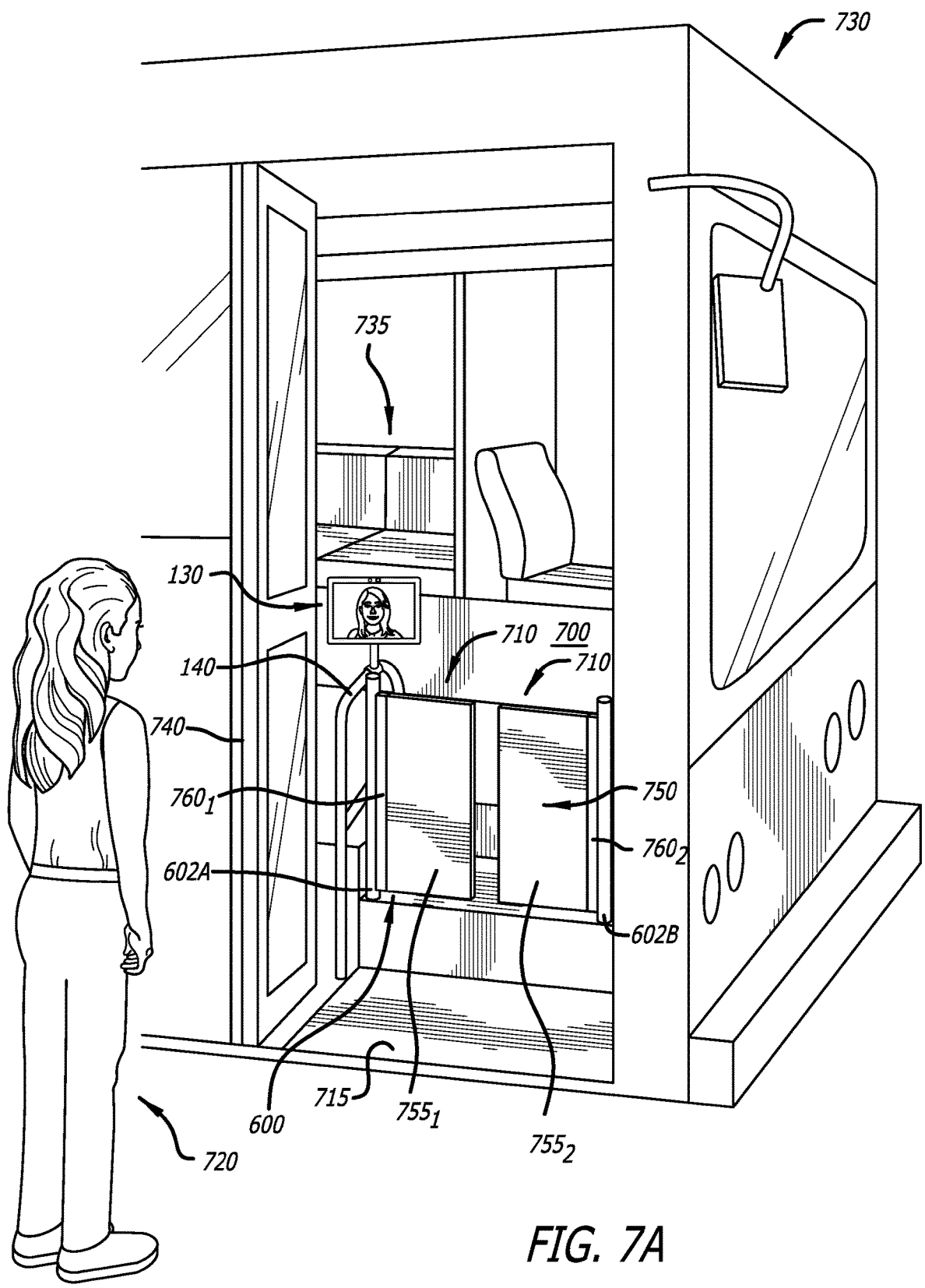
FIG. 7A is a fifth exemplary embodiment of a vehicle deploying a wellness diagnostic platform including the wellness monitoring unit along with a boarding gate that precludes boarding by any passengers with monitored symptoms of a contagious illness.

Referring to FIG. 7A, a fourth exemplary embodiment of a wellness diagnostic platform 700 is shown, which includes a mechanism 710 to control boarding of a potential passenger 720 into a vehicle 730 based on the health of the potential passenger 720. Herein, the wellness monitoring unit 130 of FIG. 1A is deployed to conduct diagnostics of the health of the potential passenger 720. Herein, the automated doors 740 are opened, but a secondary gate 750 is positioned within an interior 735 of the vehicle 730 (e.g., partially secured to the handrail 140). The secondary gate 750 is configured to preclude access by the potential passenger 720 to the interior seating 735 of the vehicle 740 when the secondary gate 750 is placed into a closed state, as shown.

As shown in FIG. 7A, the secondary gate 750 includes a first panel $755_1$ and a second panel $755_2$, which are positioned in a closed state to preclude the potential passenger 720 from entering beyond a first step of a stairway 715 providing access to the interior 735 within the vehicle 730. The first panel $755_1$ is coupled to a first vertically-oriented gate control member $760_1$ coupled to the handrail 430 while the second panel $755_2$ is coupled to a second vertically-oriented gate control member $760_2$.

Figure 7B:
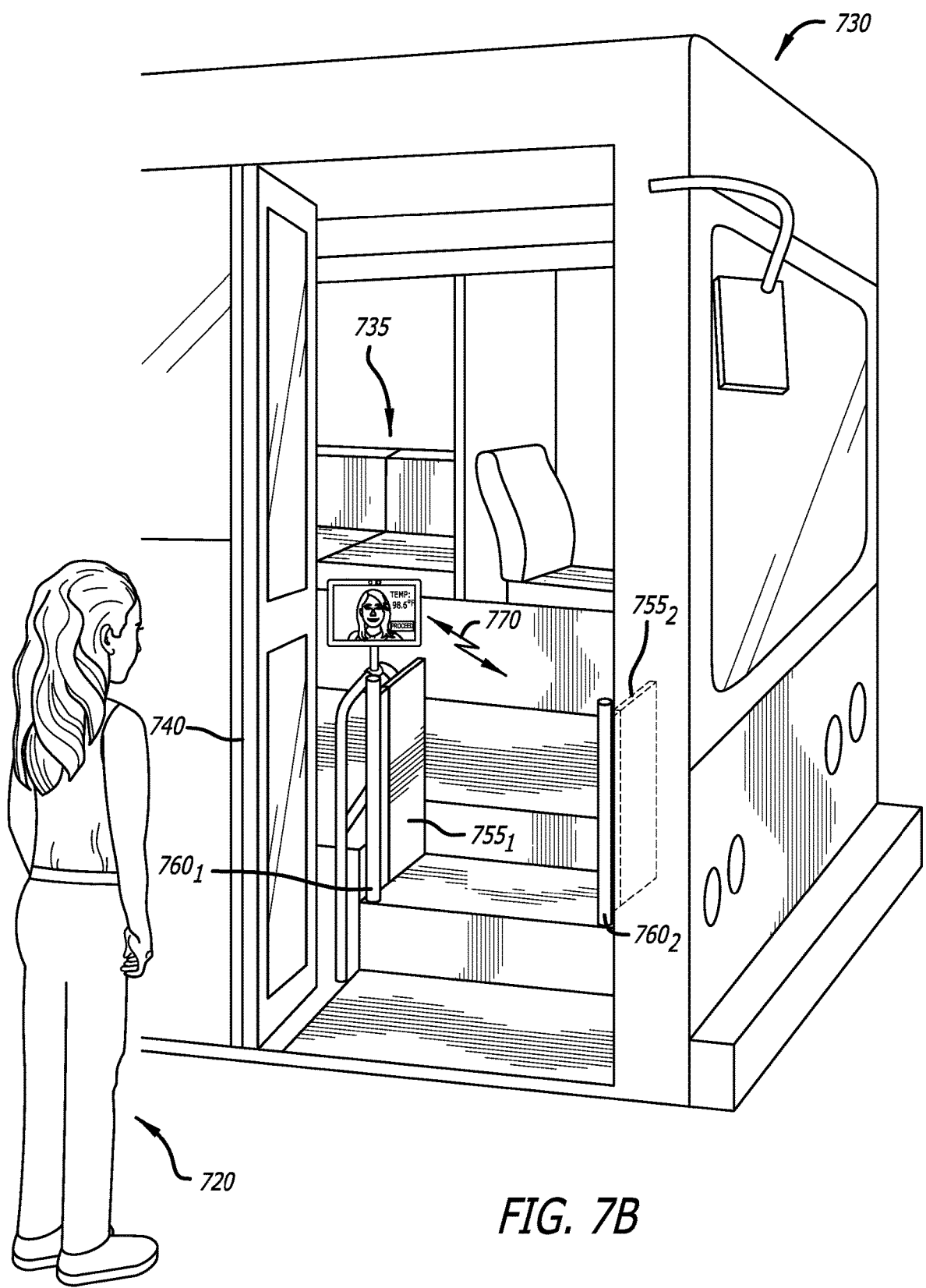
FIG. 7B is the exemplary embodiment of the boarding gate being opened to permit entry of the potential passenger into the vehicle.

Referring now to FIG. 7B, in response to the passenger being permitted to board the vehicle 730, the wellness monitoring unit 130 transmits a wireless signal 770 to both the first vertically-oriented gate control member $760_1$ and the second vertically-oriented gate control member $760_2$. The signal 770 (e.g., wired or wireless) causes the first vertically-oriented gate control member $760_1$ and the second vertically-oriented gate control member $760_2$ to rotate their corresponding panels $755_1$ and $755_2$ to allow for entry of the potential passenger 720 to gain access to the interior 735 of the vehicle 730.

In the foregoing description, the invention is described with reference to specific exemplary embodiments thereof. However, it will be evident that various modifications and changes may be made thereto without departing from the broader spirit and scope of the invention.

What is claimed is:

1. A wellness diagnostic platform installed on a vehicle to identify a potential passenger with evident symptoms of a contagious illness, comprising:

a wellness monitoring unit comprises a housing including a display screen visible from a first side of the housing, a non-transitory storage medium including control software to control operability of the wellness monitoring unit, a processor configured to execute the control software, a camera positioned on the housing, and one or more thermal sensors to measure a temperature of the potential passenger prior to boarding the vehicle, wherein the control software includes (i) a guidance subsystem configured, when executed by the processor, to generate and display indicia that (a) guides the potential passenger to reposition in front of the one or more thermal sensors and (b) includes at least a display object directing the one or more thermal sensors to measure temperature at an area near an eye of the potential passenger, and (ii) a diagnostic subsystem configured, when executed by the processor, to activate the one or more thermal sensors to conduct a thermal scan to measure the temperature of the potential passenger and determine, based on the measured temperature, whether the potential passenger is cleared to board the vehicle; and a boarding confirmation unit communicatively coupled to the wellness monitoring unit, the boarding confirmation unit to receive at least a display object identifying a diagnostic result computed by the wellness monitoring unit that the potential passenger is (i) advised to board the vehicle when a temperature of the potential passenger is equal to or below a prescribed temperature threshold or (ii) advised to refrain from boarding the vehicle when the temperature of the potential passenger exceeds prescribed temperature threshold.

2. The wellness diagnostic platform of claim 1, wherein the wellness monitoring unit advises the potential passenger to board the vehicle by at least generating and displaying a first type of display element and advises the potential passenger to refrain from boarding the vehicle by at least generating and displaying a second type of display element.

3. The wellness diagnostic platform of claim 1, wherein the camera is positioned on a bezel of the housing and the one or more thermal sensors positioned on the bezel.

4. The wellness diagnostic platform of claim 3, wherein a back side of the housing includes a bracket for securely couple to a fastener attached to a rail positioned proximate to a door of the vehicle.

5. The wellness diagnostic platform of claim 1, wherein the indicia further includes one or more display objects that are rendered to overlay a facial image of the potential passenger as captured by the camera.

6. A wellness monitoring unit installed on a vehicle to identify a potential passenger with evident symptoms of a contagious illness, comprising:
    a housing including a camera mounted to the housing to generate one or more images of the potential passenger;
    a display screen partially enclosed within and visible from the housing;
    one or more thermal sensors mounted on the housing;
    a processor; and
    a non-transitory storage medium including control software to control operability of the wellness monitoring unit to activate the one or more sensors to measure a temperature of the potential passenger when the potential passenger is appropriate positioned in front of the display screen and conduct diagnostics of the measured temperature to determine whether to generate a first type of display element that signifies to the potential passenger to board the vehicle or generate a second type of display element that signifies to the potential passenger to refrain from boarding the vehicle, the control software including a guidance subsystem and a diagnostic subsystem
    wherein the processor is configured to execute the guidance subsystem to generate and display indicia that guides the potential passenger to reposition in front of the one or more thermal sensors and the processor is further configured to execute the diagnostic subsystem to activate the one or more thermal sensors to conduct a thermal scan to measure the temperature of the potential passenger and determine, based on the measured temperature, whether the potential passenger is cleared to board the vehicle, and
    wherein the indicia includes one or more display objects that are rendered to overlay a facial image of the potential passenger as captured by the camera and at least one of the one or more display objects directs a thermal sensor of the one or more thermal sensors to measure temperature at an area near an eye of the potential passenger.

7. The wellness monitoring unit of claim 6 being mounted on a side panel of the vehicle.

8. The wellness monitoring unit of claim 6, wherein the camera is mounted on a bezel of the housing, the camera to generate images of the potential passenger.

9. The wellness monitoring unit of claim 6, wherein a back side of the housing includes a bracket for securely couple to a fastener attached to a rail positioned proximate to a door of the vehicle.

10. A wellness diagnostic platform installed on a vehicle to identify potential passengers with evident symptoms of a contagious illness, comprising:
    a wellness monitoring unit comprises a housing including a display screen visible from a first side of the housing, one or more thermal sensors to measure a temperature of the potential passenger prior to boarding the vehicle, and at least one or more cameras to capture at least one image associated with one or more physical characteristics of the potential passenger and conduct analytics on the captured physical characteristic or physical characteristics to determine whether analytic results conclude that the potential passenger has the contagious illness prior to boarding the vehicle, wherein the wellness monitoring unit further comprises a guidance software subsystem configured to generate and display indicia that (a) guides the potential passenger to reposition in front of the one or more thermal sensors and (b) includes at least a display object directing a thermal sensor of the one or more thermal sensors to measure temperature at an area near an eye of the potential passenger; and
    a boarding confirmation unit communicatively coupled to the wellness monitoring unit, the boarding confirmation unit to receive at least a display object identifying a diagnostic result computed by the wellness monitoring unit that the potential passenger is (i) advised to board the vehicle when the wellness monitoring unit determines that the potential passenger is well after the analytic result determine that the potential passenger does not have the contagious illness or (ii) advised to refrain from boarding the vehicle when the potential passenger is determined to have the contagious illness.

11. The wellness diagnostic platform of claim 10, wherein the wellness monitoring unit comprises a diagnostic subsystem to conduct analytics on the at least one captured image.

12. The wellness diagnostic platform of claim 10, wherein the one or more physical characteristics are directed to characteristics associated with a skin, eyes or mouth of the potential passenger.

13. The wellness diagnostic platform of claim 10, wherein the one or more physical characteristics are directed to one or more of the following: (i) pale lips visually discerned from a facial image correspond to the at least one captured image, (ii) pale skin visually discerned from the facial image, (iii) a swollen face visually discerned from the facial image, (iv) droopy corners of a mouth of the potential passenger visually discerned from the facial image, (v) hanging eyelids visually discerned from the facial image, or (vi) discolored (red) eyes visually discerned from the facial image.

* * * * *